(12) United States Patent
Meazza et al.

(10) Patent No.: US 6,391,827 B1
(45) Date of Patent: May 21, 2002

(54) PYRROLIC COMPOUNDS HAVING A HIGH HERBICIDAL ACTIVITY AND THEIR AGRONOMIC USE

(75) Inventors: Giovanni Meazza, Saronno; Franco Bettarini, Novara; Paolo Castoro, Vercelli; Piero La Porta, Novara; Ernesto Signorini, Malnate; Domenico Portoso, Lodi, all of (IT)

(73) Assignee: Isagro Ricerca S.r.l., Milan (IT)

( * ) Notice: Subject to any disclaimer, the term of this patent is extended or adjusted under 35 U.S.C. 154(b) by 0 days.

(21) Appl. No.: 09/594,156

(22) Filed: Jun. 15, 2000

(30) Foreign Application Priority Data

Aug. 17, 1999  (IT) .......................... MI99A1347

(51) Int. Cl.⁷ ...................... A01N 43/36; C07D 207/32
(52) U.S. Cl. ...................... 504/283; 548/562
(58) Field of Search .................. 504/283; 548/562

(56) References Cited

U.S. PATENT DOCUMENTS 4,495,196 A * 1/1985 Boswell, Jr. ............... 514/427

FOREIGN PATENT DOCUMENTS

| EP | 0 312 723 | 4/1989 |
| EP | 0 351 641 | 1/1990 |
| EP | 0 358 047 | 3/1990 |
| EP | 0 369 262 | 5/1990 |
| EP | 0 481 182 | 4/1992 |
| GB | 1127929   | 9/1968 |

OTHER PUBLICATIONS

Chemical Abstracts, AN 51988k, Sep. 23, 1968, JP 42 025888, Dec. 9, 1967.
Chemical Abstracts, AN 115598f, Jun. 19, 1967, JP 42 000184, Jan. 9, 1967.
Patent Abstracts of Japan, vol. 1995, No. 11, Dec. 26, 1995, JP 7 196608, Aug. 1, 1995.

* cited by examiner

Primary Examiner—Floyd D. Higel
Assistant Examiner—Sonya Wright
(74) Attorney, Agent, or Firm—Oblon, Spivak, McClelland, Maier & Neustadt, P.C.

(57) ABSTRACT

The invention relates to pyrrolic compounds having formula (I)

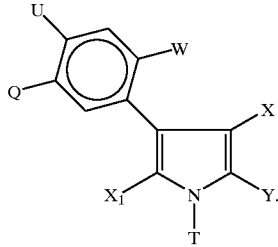

The compounds having formula (I) have a high herbicidal activity and are used for controlling weeds in the agronomic field

13 Claims, No Drawings

PYRROLIC COMPOUNDS HAVING A HIGH HERBICIDAL ACTIVITY AND THEIR AGRONOMIC USE

The present invention relates to new pyrrolic compounds having a herbicidal activity.

More specifically, the present invention relates to pyrrolic compounds having a high herbicidal activity, the process for their preparation and their use as herbicides for controlling weeds in agricultural crops. Pyrroles with a herbicidal activity are described, for example, in European patent application EP 351,641.

Pyrroles with a herbicidal activity are also described in patent application EP 369,262.

The Applicant has now found new pyrrolic compounds which, in addition to having an excellent herbicidal activity with respect to numerous weeds, also have limited toxicity towards various crops of agrarian interest and can therefore be used as selective herbicides.

The object of the present invention consequently relates to pyrrolic compounds having general formula (I)

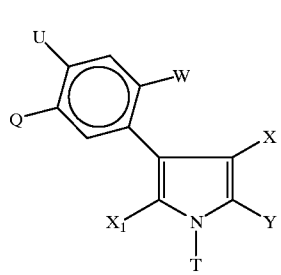

(I)

wherein:
W represents a hydrogen, fluorine or chlorine atom;
U represents a halogen atom, an alkyl, haloalkyl group, a cyano group, a nitro group;
represents a hydrogen atom, a halogen atom, a $C_1$–$C_8$ alkyl group, a $C_1$–$C_8$ halogenalkyl group, a $C_3$–$C_6$ cycloalkyl group, a $C_4$–$C_8$ cycloalkylalkyl group, an alkenyl group, said groups can in turn be further substituted by one or more substituents selected from halogen atoms, $C_1$–$C_4$ alkoxyl groups, $C_1$–$C_4$ haloalkoxyl groups, $C_1$–$C_4$ alkylthio groups, $C_1$–$C_4$ haloalkylthio groups, $C_1$–$C_4$ alkylsulfinic groups, $C_1$–$C_4$ haloalkylsulfinic groups, $C_1$–$C_4$ alkylsulfonic groups, haloalkylsulfonic groups;
or it represents a ZR, $COR_1$, $CO_2R_2$, $CH_2CHR_3CO_2R_2$, $CH=CHR_3CO_2R_2$, $CR_4=NOR_5$, $CO-NR_6R_7$, CN, $NO_2$, $NR_8R_9$, $NR_{10}SO_2R_{11}$, $N(SO_2R_{11})_2$, $NR_{12}-CO-R_{13}$, $NR_{14}-CO-OR_{15}$, $NR_{16}-CO-NR_{17}R_{18}$ group; Groups U and Q can be joined to each other by means of saturated carbon atoms and/or unsaturated carbon atoms, and/or $C=Z_1$ groups, and/or oxygen atoms, and/or $S(O)_m$ groups, and/or $NR_{19}$ groups to form cyclic rings having up to 9 members, in which the carbon atoms can be substituted with one or more $C_1$–$C_4$ alkyl or haloalkyl groups;
T represents a hydrogen atom, a $C_1$–$C_8$ alkyl or haloalkyl group, a $C_1$–$C_8$ alkoxyalkyl or haloalkoxyalkyl group, a $Z_2R_{11}$ group;
X represents a hydrogen atom, a halogen atom, a $C_1$–$C_8$ halogenalkyl group, a $CO_2R_{21}$ group, a $CO-NR_6R_7$ group;
$X_1$ represents a hydrogen atom, a halogen atom, a $C_1$–$C_8$ halogenalkyl group, a cyano group, a $CO_2R_{22}$ group, a $CO-NR_6R_7$ group;

Y represents a $C_1$–$C_8$ alkyl or haloalkyl group, a cyano group, a $Z_3Y_1$ group;
$Y_1$ represents a $C_1$–$C_8$ alkyl or haloalkyl group;
Z, $Z_2$, $Z_3$ represent O or S(O)n wherein n=0–1;
$Z_1$ represents O or S
m=0–2
R represents a hydrogen atom, a $C_1$–$C_8$ alkyl group, a $C_3$–$C_6$ cycloalkyl group, a $C_4$–$C_8$ cycloalkylalkyl group, a $C_{2-C8}$ alkenyl group, a $C_2$–$C_8$ alkynyl group, an aryl group, an arylalkyl group, a heterocyclic group with 5 or 6 terms containing from 1 to 4 heteroatoms, the same or different, selected from N, O, S, a heterocyclylalkyl group; said groups can in turn be further substituted by one or more substituents selected from halogen atoms, $C_1$–$C_4$ alkoxyl groups, $C_1$–$C_4$ haloalkoxyl groups, $C_1$–$C_4$ alkylthio groups, $C_{1-C4}$ haloalkylthio groups, $C_1$–$C_4$ alkylsulfinic groups, $C_1$–$C_4$ haloalkylsulfinic groups, $C_1$–$C_4$ alkylsulfonic groups, $C_1$–$C_4$ haloalkylsulfonic groups, COOH groups, $C_2$–$C_6$ alkoxycarbonyl groups, $C_2$–$C_6$ haloalkoxycarbonyl groups, $C_3$–$C_8$ alkoxycarbonylcarbonyl groups, $C_3$–$C_8$ haloalkoxycarbonylcarbonyl groups, $C_2$–$C_6$ alkylaminocarbonyl groups, $C_3$–$C_9$ dialkylaminocarbonyl groups, $C_3$–$C_7$ alkylaminocarbonylcarbonyl groups, $C_4$–$C_{10}$ dialkylaminocarbonylcarbonyl groups, $C_2$–$C_6$ alkylcarbonyl groups, $C_2$–$C_6$ aloalkylcarbonyl groups, $C_3$–$C_8$ alkoxyiminoalkyl groups, $C_4$–$C_8$ alkoxyiminohaloalkyl groups, CHO groups, CN groups, $NO_2$ groups;
$R_1, R_2, R_4, R_5, R_{10}, R_{11}, R_{12}, R_{13}, R_{14}, R_{15}, R_{16}, R_{19}, R_{20}, R_{21}, R_{22}$, represent a hydrogen atom, or a $C_1$–$C_6$ alkyl or haloalkyl group, a $C_3$–$C_6$ cycloalkyl group, a $C_7$–$C_{12}$ arylalkyl group or an aryl group, said arylalkyl and aryl groups also optionally substituted;
$R_3$ represents a hydrogen atom, a halogen atom, or a $C_1$–$C_2$ alkyl or haloalkyl group;
$R_6, R_7$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also optionally substituted, or they jointly represent a $C_2$–$C_5$ alkylene chain;
$R_8, R_9$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also optionally substituted, or they jointly represent a $C_2$–$C_5$ alkylene chain;
$R_{17}, R_{18}$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also optionally substituted, or they jointly represent a $C_2$–$C_5$ alkylene chain.

The pyrroles having general formula (I) have a high herbicidal activity.

Specific examples of arylpyrroles having general formula (I) which are of interest for their herbicidal activity are:
ethyl 5-(2,4-dibromo-1-methyl-5-trifluoromethyl pyrrol-3-yl)-2-chloro-4-fluorophenoxyacetate;
ethyl 5-(2,4-dichloro-1-methyl-5-trifluoromethyl pyrrol-3-yl)-2-chloro-4-fluorophenoxyacetate;
ethyl 2-chloro-5-(4-bromo-2-chloro-1-methyl-5-trifluoromethylpyrrol-3-yl)-4-fluorophenoxyacetate;
ethyl 2-chloro-5-(2-bromo-1-methyl-5-trifluoro methyl pyrrol-3-yl)-4-fluorophenoxyacetate;
3-[4-chloro-2-fluoro-5-(2-propinyloxy)phenyl]-2,4-dibromo-1-methyl-5-trifluoromethylpyrrole;

3-[4-chloro-2-fluoro-5-(2-propinyloxy)phenyl]-2,4-dichloro-1-methyl-5-trifluoromethylpyrrole;
4-bromo-3-[4-chloro-2-fluoro-5-(2-propinyloxy)phenyl]-2-chloro-1-methyl-5-trifluoromethylpyrrole;
2-bromo-3-[4-chloro-2-fluoro-5-(2-propinyloxy)phenyl]-1-methyl-5-trifluoromethylpyrrole;
methyl 2-chloro-5-(2,4-dibromo-1-methyl-5-trifluoromethyl pyrrol-3-yl)-4-fluorobenzoate;
1-methylethyl 2-chloro-5-(2,4-dibromo-1-methyl-5-trifluoro methylpyrrol-3-yl)-4-fluorobenzoate;
ethyl 2-chloro-5-(2,4-dibromo-1-methyl-5-trifluoromethyl pyrrol-3-yl)-4-fluorobenzoate;
N,N-dimethyl 2-chloro-5-(2,4-dibromo-1-methyl-5-trifluoro methylpyrrol-3-yl)-4-fluorobenzamide;
1- [2-chloro-5- (2,4-dibromo-1-methyl-5-trifluoro methylpyrrol-3-yl)-4-fluorobenzoyl]pyrrolidine;
4-chloro-3-(2,4-dichloro-5-nitrophenyl)-1-methyl-5-trifluoromethylpyrrole-2-carbonitrile;
N-[5-(2-cyano-4-chloro-1-methyl-5-trifluoromethylpyrrol-3-yl)-2,4-dichlorophenyl]bismethylsulfonamide;
N-[5-(2-cyano-4-chloro-1-methyl-5-trifluoromethylpyrrol-3-yl)-2,4-dichlorophenyl]methylsulfonamide.

A further object of the present invention relates to processes for the preparation of the compounds having general formula (I).

The pyrroles having general formula (I) can be prepared according to methods known to experts in the field and in particular by adapting to the specific substrates necessary, the known methods described in literature such as, for example, by G. P. Bean in "The Chemistry of Heterocyclic Compounds" "Pyrroles" (1990), vol. 1, chap. 2, pages 105–294 Ed. Wiley-New York and by R. G. Sundberg in "Comprehensive Heterocyclic Chemistry" (1984), vol. IV, chap. 5, pages 313–376.

More specifically, the compounds having general formula (I) can be prepared, for example, by reacting alkynes having general formula II:

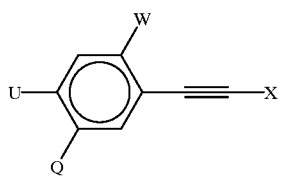

(II)

with aminoacid derivatives having general formula (III)

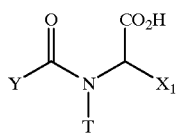

(III)

The reaction can be carried out in an inert organic solvent and in the presence of a dehydrating agent, at a temperature ranging from 50° C. to the boiling point of the reaction mixture.

Examples of solvents suitable for the embodiment of the process are: benzene, toluene, xylene.

Examples of suitable dehydrating. agents are acetic anhydride, propionic anhydride, butyric anhydride, dicyclohexylcarbodiimide (DCC).

The above is in accordance with what is described, for example, in "Journal of Organic Chemistry" (1977), vol. 42, pages 559–561; "Journal of Organic Chemistry" (1979), vol. 44, pages 977–979; "Journal of Organic Chemistry" (1982), vol. 47, pages 786–791.

Another process consists in reacting a compound having general formula (III) with an alkene having general formula (IV), wherein L represents an outgoing group such as chlorine, bromine, cyano;

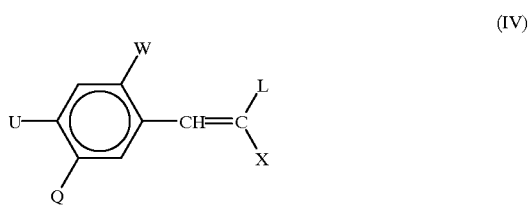

(IV)

according to what is described, for example, in "Tetrahedron Letters" (1983), vol. 24, pages 369–372.

Another process consists in reacting an alkyne having general formula (II) or an alkene having general formula (IV) with an azalactone having general formula (V)

(V)

according to what is described, for example, in "Journal of Organic Chemistry" (1978), vol. 43, pages 4273–4276; "Tetrahedron" (1986), vol. 42, pages 5857–5862; "Bulletin SociétéChimique de France" (1983), pages 195–201.

A further process consists in reacting compounds having general formula (VI)

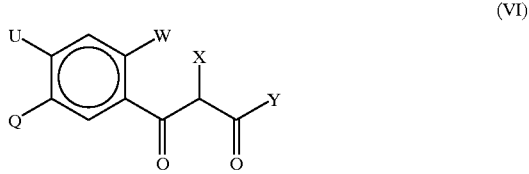

(VI)

with a compound having general formula (VII) or with one having general formula (VIII):

(VII)

(VIII)

to give compounds having general formula (I) wherein T represents hydrogen and $X_1$ represents a $CO_2R_{22}$ group, according to what is described, for example, in "Journal of American Chemical Society" (1955), vol. 77, pages 1546–1548; "Synthesis" (1982), pages 157–159.

Another process consists in reacting compounds having general formula (IX)

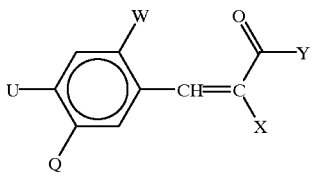
(IX)

with a compound having general formula (X)

$X_1$—$CH_2NO_2$ (X)

to give intermediate compound having general formula (XI)

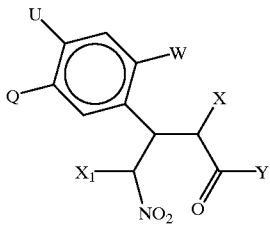
(XI)

which can be transformed (after reduction of the nitro group) into the compounds having general formula (I) wherein T presents a hydrogen atom, according to what is described, for example, in "Tetrahedron Letters" (1995), vol. 36, pages 9469–9470; "Tetrahedron Letters" (1984), vol. 25, pages 3707–3710; "Journal of the Chemical Society Perkin Transactions 1" (1986), pages 2243–2252.

The intermediate compounds having general formula (XI) can be oxidized, for example with ozone, to give the intermediate compounds having general formula (XII)

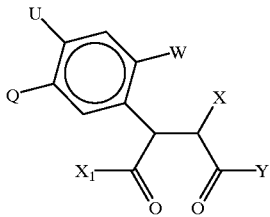
(XII)

which by reaction with compounds having general formula (XIII)

T—$NH_2$ (XIII)

can be transformed into compounds having general formula (I) wherein T can be different from a hydrogen atom.

The reaction can be carried out according to what is described, for example, in "Journal of Organic Chemistry" (1983), vol. 48, pages 2769–2772.

Compounds having general formula (I) wherein Y represents a $ZY_1$ group, where Z represents an oxygen atom, can be prepared, starting from intermediates having general formula (XI) and (XII), according to the procedures described above. Intermediate compounds having general formula (XIV) are obtained

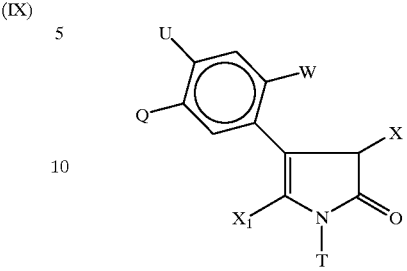
(XIV)

which are subsequently reacted with a compound having general formula (XV)

$Y_1$—$L_1$ (XV)

wherein $L_1$ represents an outgoing group such as chlorine, bromine, mesyl, according to the procedure described, for example, in "Journal of Organic Chemistry" (1982), vol. 47. Pages 1750–1754.

The alkynes having general formula (II) can be prepared according to methods known to experts in the field and in particular by adapting to the specific substrates necessary, known methods described in literature such as, for example, by L. Brandsma in "Preparative cetylenic Chemistry" (1988), $II^{nd}$ Ed. Elsevier-Amsterdam. More specifically, the compounds having general formula (II) can be prepared according to the procedures indicated in: "Journal of Organic Chemistry" (1981), vol. 46, pages 2280–2286; "Synthesis" (1980), pages 627–630; "Synthesis" (1996) pages 589–590; "Journal of Organic Chemistry" (1997), vol. 62, pages 8957–8960.

The alkenes having general formula (IV) can be prepared by adapting to the specific substrates necessary, known methods described in literature such as, for example, in "Organic Reactions" (1976), vol. 24, pages 225–259; "Organic Reactions" (1982), vol. 27, pages 345–390; "Organic Reactions" (1965), vol. 14, pages 270–490.

The azalactones having general formula (V) can be prepared by adapting to the specific substrates necessary, known methods described in literature such as, for example, in "Chemische Berichte" (1970), vol. 103, pages 2611–2624 and "Liebig Annalen der Chemie" (1926), vol 449, pages 277–302.

The compounds having general formula (VI) can be prepared by adapting to the specific substrates necessary, known methods described in literature such as, for example, in "Chemical Reviews" (1995), vol. 95, pages 1065–1114; "Russian Chemical Reviews" (1981), vol. 50, pages 325–354.

The compounds having general formula (IX) can be prepared by following the procedures indicated, for example, in "Organic Reactions" (1942), vol. 1, pages 1–37; "Tetrahedron Letters" (1985), vol. 26, pages 2873–2876; "Journal of the Chemical Society Perkin Transactions 1" (1995), pages 741–742.

The compounds having general formula (III), (VII), (VIII), (X), (XIII) and (XV) can be commercially available products, or products whose preparation is described in literature, and in any case can be easily prepared with general methods well known to experts in the field.

The pyrroles obtained, for example, with the methods described above, can be subsequently processed in order to obtain pyrroles having formula (I) additionally and/or differently substituted.

This subsequent processing can relate either to the pyrrole ring or to the aryl ring.

The modifications relating to the pyrrole ring can be effected according to methods known to experts in the field, described for example by various authors in "The Chemistry of Heterocyclic Compounds" "Pyrroles" (1990), vol. 1, chap. 3, pages 295–548 Ed. Wiley-New York e by R. A. Jones in "Comprehensive Heterocyclic Chemistry" (1984), vol. IV, chap. 4, pages 201–312.

For example, pyrroles (I) wherein X and $X_1$ are hydrogen atoms, obtained using the methods described above, can be transformed into pyrroles (I) wherein $X_1$ is a bromine atom, by treatment with 1 equivalent of bromine in dioxane or with 1 equivalent of N-bromosuccinimide in THF or DMF. Using two or more equivalents of the brominating reagents mentioned above, pyrroles (I) are obtained wherein $X_1$ and X are both bromine atoms. By adopting a chlorinating agent such as N-chlorosuccinimide, it is possible to obtain pyrroles (I) wherein, in relation to the stoichiometric ratios used, $X_1$ alone or $X_1$ and X are both chlorine atoms.

Furthermore, it is possible, for example, to transform pyrroles (I), wherein $X_1$ and X represent two bromine atoms, into pyrroles (I) wherein $X_1$ is a chlorine atom and X is a bromine atom by treatment with 1 equivalent of $SO_2C_{12}$.

The compounds having general formula (I) object of the present invention, have shown a high herbicidal activity which makes them suitable for use in the agrarian field to defend useful crops from weeds.

In particular, the compounds having general formula (I) are effective in controlling numerous monocotyledon and dicotyledon weeds, both in pre-emergence and post-emergence applications.

At the same time, these compounds show compatibility or absence of toxic effects with respect to useful crops. Examples of weeds which can be effectively controlled using the compounds having general formula (I) object of the present invention, are: *Amni maius, Abutilon theofrasti, Stellaria media, Convolvulus sepium, Amaranthus retroflexus, Chenopodium album, Galium aparine, Solanum nigrum, Portulaca oleracea, Sida spinosa, Sorgum halefense, Echinicloa crusgalli, Averia fatua, Alogecurus myosuroides*, etc.

At the doses used for agrarian applications, the above compounds do not have any toxic effects with respect to important crops such as rice (*Oryza sativa*), wheat (*Triticum* spp.), maize (*Zea mais*), soybean (*Glicine max*), etc.

A further object of the present invention relates to a method for controlling weeds in cultivated areas by the application of the compounds having general formula (I).

The quantity of compound to be applied to obtain the desired effect can vary in relation to various factors such as, for example, the compound used, the crop to be preserved, the weed to be attacked, the degree of infestation, the climatic conditions, the characteristics of the soil, the application method, etc.

Doses of compound ranging from 1 to 1000 g per hectare generally provide sufficient control.

For practical use in agriculture, it is often advantageous to use compositions with a herbicidal activity containing, as active substance, one or more of the compounds having general formula (I). Compositions can be used in the form of dry powders, wettable powders, emulsifiable concentrates, micro-emulsions, pastes, granulates, solutions, suspensions, etc.: the selection of the type of composition will depend on the specific use.

The compositions are prepared according to known methods, for example by diluting or dissolving the active substance with a solvent medium and/or solid diluent, optionally in the presence of surface-active agents.

Solid inert diluents, or carriers, which can be used are kaolin, alumina, silica, talc, bentonite, chalk, quartz, dolomite, attapulgite, montmorillonite, diatomaceous earth, cellulose, starch, etc.

Liquid inert diluents which can be used are water, or organic solvents such as aromatic hydrocarbons (xylols, mixtures of alkylbenzenes, etc.), aliphatic hydrocarbons (hexane, cyclohexane, etc.), halogenated aromatic hydrocarbons (chlorobenzene, etc.), alcohols (methanol, propanol, butanol, octanol, etc.), esters (isobutyl acetate, ect.), ketones (acetone, cyclohexanone, acetophenone, isophorone, ethylamylketone, etc.), or vegetable or mineral oils or their mixtures, etc.

Surface-active agents which can be used are wetting and emulsifying agents of the non-ionic type (polyethoxylated alkylphenols, polyethoxylated fatty alcohols, etc.), anionic type (alkylbenzenesulfonates, alkylsulfonates, etc.), cationic type (alkylammonium quaternary salts etc.).

Dispersing agents (for example lignin and its salts, derivatives of cellulose, alginates, etc.), stabilizers (for example antioxidants, U.V. absorbers, etc.) can also be added.

To widen the range of action of the above compositions, it is possible to add other active ingredients such as, for example, other herbicides, fungicides, insecticides or acaricides, fertilizers.

Examples of other herbicides which can be added to the compositions containing one or more compounds having general formula (I) are the following: acetochlor, acifluorfen, aclonifen, AKH-7088, alachlor, alloxydim, ametryn, amidosulfuron, amitrole, anilofos, asulam, atrazine, azafenidin (DPX-R6447), azimsulfuron (DPX-A8947), aziprotryne, benazolin, benfluralin, benfuresate, bensulfuron, bensulide, bentazone, benzofenap, benzthiazuron, bifenox, bilanafos, bispyribac-sodium (KIH-2023), bromacil, bromobutide, bromofenoxim, bromoxynil, butachlor, butamifos, butenachlor, butralin, butroxydim, butylate, cafenstrole (CH-900), carbetamide, carfentrazone-ethyl (F8426), chlomethoxyfen, chloramben, chlorbromuron, chlorbufam, chlorflurenol, chloridazon, chlorimuron, chlornitrofen, chlorotoluron, chloroxuron, chlorpropham, chlorsulfuron, chlorthal, chlorthiamid, cinidon ethyl, cinmethylin, cinosulfuron, clethodim, clodinafop, clomazone, clomeprop, clopyralid, cloransulam-methyl (XDE-565), cumyluron (JC-940) cyanazine, cycloate, cyclosulfamuron (AC-322140), cycloxydim, cyhalofop-butyl (XDE-537), 2,4-D, 2,4-DB, daimuron, dalapon, desmedipham, desmetryn, dicamba, dichlobenil, dichlorprop, dichlorprop-P, diclofop, diclosulam (XDE-564), diethatyl, difenoxuron, difenzoquat, diflufenican, diflufenzopyr (SAN 835H), dimefuron, dimepiperate, dimethachlor, dimethametryn, dimethenamid, dinitramine, dinoseb, dinoseb acetate, dinoterb, diphenamid, dipropetryn, diquat, dithiopyr, 1-diuron, eglinazine, endothal, epoprodan (MK-243), EPTC, esprocarb, ethalfluralin, ethametsulfuron-methyl (DPX-A7881), ethidimuron, ethiozin (SMY 1500), ethofumesate, ethoxyfen-ethyl (HC-252), ethoxysulfuron (HOE 095404), etobenzanid (HW 52), fenoxaprop, fenoxaprop-P, fentrazamide (BAY YRC 2388), fenuron, flamprop, flamprop-M, flazasulfuron, fluazifop, fluazifop-P, fluchloralin, flumetsulam (DE-498),flumiclorac-pentyl, flumioxazin, flumipropin, fluometuron, fluoroglycofen, fluoronitrofen, flupoxam, flupropanate, flupyrsulfuron (DPX-KE459), flurenol, fluridone, flurochloridone, fluroxypyr, flurtamone, fluthiacetmethyl (KIH-9201), fluthiamide (BAY FOE 5043), fomesafen, fosamine, furyloxyfen, glufosinate, glyphosate, halosulfuron-methyl (NC-319), haloxyfop, haloxyfop-P-methyl, hexazinone, imazamethabenz, mazamox (AC-299263), imazapic (AC-263222), imazapyr, imazaquin, imazethapyr, imazosulfuron, ioxynil, isopropalin, isopropazol (JV 485), isoproturon, isouron, isoxaben, isoxaflutole (RPA 201772), isoxapyrifop, KPP-421, lactofen, lenacil, linuron, LS830556, MCPA, MCPA-thioethyl, MCPB, mecoprop, mecoprop-P, mefenacet, metamitron, metazachlor, methabenzthiazuron, methazole, methoprotryne, methyldymron, metobenzuron, metobromuron, metolachlor, metosulam (DE-511), metoxuron, metribuzin, metsulfuron, molinate, monalide, monolinuron, naproanilide, napropamide, naptalam, NC-330, neburon, nicosulfuron, nipyraclofen, norflurazon, orbencarb, oryzalin, oxadiargyl, oxadiazon, oxasulfuron (CGA-277476), oxaziclomefone (MY-100), oxyfluorfen, paraquat, pebulate, pendimethalin, pentanochlor, pentoxazone (KPP-314), phenmedipham, picloram, piperophos, pretilachlor, primisulfuron, prodiamine, proglinazine, prometon, prometryne, propachlor, propanil, propaquizafop, propazine, propham, propisochlor, propyzamide, prosulfocarb, prosulfuron (CGA-152005), pyraflufenethyl (ET-751), pyrazolynate, pyrazosulfuron, pyrazoxyfen, pyribenzoxim (LGC-40863), pyributicarb, pyridate, pyriminobac-methyl (KIH-6127), pyrithiobac-sodium (KIH-2031), quinclorac, quinmerac, quizalofop, quizalofop-P, rimsulfuron, sethoxydim, siduron, simazine, simetryn, sulcotrione, sulfentrazone (F6285) sulfometuron (DPX-5648), sulfosulfuron (MON 37500), 2,3,6-TBA, TCA-sodium, tebutam, tebuthiuron, tepraloxydim (BAS 620H), terbacil, terbumeton, terbuthylazine, terbutryn, thenylchlor (NSK-850), thiazafluron, thiazopyr (MON 13200), thidiazimin, thifensulfuron, thiobencarb, tiocarbazil, tioclorim, tralkoxydim, tri-allate, triasulfuron (CGA-131036), triaziflam (IDH-1105), tribenuron, triclopyr, trietazine, trifluralin, triflusulfuron-methyl (DPX-66037), UBI-$C_{4874,}$ vernolate.

The concentration of active substance in the above compositions can vary within a wide range, depending on the active compound, applications for which they are destined, environmental conditions and type of formulation adopted.

The concentration of active substance generally ranges from 1 to 90%, preferably from 5 to 50%.

The following examples are provided for illustrative purposes but do not limit the scope of the present invention.

In the nuclear magnetic resonance spectra indicated in the examples, the following abbreviations were used: s=singlet; d=doublet; t=triplet; q=quartet; bs=enlarged singlet; m=multiplet or complex signal.

EXAMPLE 1

Preparation of 4-(4-chloro-2-fluoro-5-acetoxyphenyl)-1-methyl-2-trifluoromethylpyrrole (Compound Nr. 1)

Acetic anhydride (2 ml) is added to a suspension of 2-chloro-4-fluoro-5-ethinylphenol (1 g; 5.9 mmoles) and N-trifluoroacetyl sarcosine (1.08 g; 5.9 mmoles) in xylene (10 ml). The mixture is heated to 130° C. for 25 hours. The reaction mixture is poured into water (10 ml), extracted with ethyl ether (3×20 ml), the ether phase is washed with a saturated solution of sodium chloride, anhydrified with sodium sulfate and concentrated in a rotavapor. The raw product obtained (2 g) is chromatographed on silica gel, eluating with hexane/ethyl acetate 85:15. 1.0 g of solid white product are obtained.

$^1$H-NMR (CDCl$_3$): δ at 2.35 (s, 3H, CH$_3$CO); 3.75 (bs, 3H, NCH$_3$); 6.86–6.81 (m, 1H, pyrrole); 7.12–7.26 (m, 3H, aromatics and pyrrole).

$^{19}$F-NMR (CDCl$_3$): δ at −116.7 (m, 1F, aromatic); −59.4 (s, 3F, CF$_3$)

EXAMPLE 2

Preparation of 3-(4-chloro-2-fluoro-5-hydroxyphenyl)-2,4-dibromo-1-methyl-5-trifluoromethylpyrrole (Compound Nr. 2)

A solution of bromine (2.9 g; 17.9 mmoles) in dioxane (20 ml) are dripped into a solution of 4-(4-chloro-2-fluoro-5-acetoxyphenyl)-1-methyl-2-trifluoromethylpyrrole (2.0 g; 5.9 mmoles) in dioxane (10 ml). The mixture is maintained under stirring at room temperature for 48 hours. After evaporation of the solvent in a rotavapor, ethyl ether (50 ml) is added to the residue, the mixture is washed with a saturated solution of sodium metabisulfite (20 ml) and then with water, anhydrified with sodium sulfate and concentrated in a rotavapor. The reaction raw product (3.7 g) dissolved in a mixture of methanol/water 2:1 (40 ml) is treated with potassium carbonate (1.5 g) The solution is kept under stirring at room temperature for 3 hours. The reaction mixture is diluted with ethyl ether (100 ml), the ether phase is washed with a solution of hydrochloric acid at 5%, and is then washed until neutral pH with a saturated solution of sodium chloride, anhydrified with sodium sulfate and concentrated in a rotavapor. 2.8 g of product are obtained in the form of brown oil.

$^1$H-NMR (CDCl$_3$): δ at 3.78 (bs, 3H, NCH$_3$); 5.68 (bs, 1H, OH); 6.93 (d, 1H, aromatic); 7.18 (d, 1H, aromatic).

$^{19}$F-NMR (CDCl$_3$): δ at −120.9 (m, 1F, aromatic); −57.0 (s, 3F, CF$_3$).

EXAMPLE 3

Operating analogously to the procedure described in example 2, the following compound was prepared starting from 4-(4-chloro-2-fluoro-5-acetoxyphenyl)-1-methyl-2-trifluoromethylpyrrole and an equimolar quantity of bromine: -2-bromo-3-(4-chloro-2-fluoro-5-hydroxyphenyl)-1-methyl-5-trifluoromethylpyrrole (compound Nr. 3). GC-MS: m/e 371.

EXAMPLE 4

Preparation of ethyl 2-chloro-5-(2,4-dibromo-1-methyl-5-trifluoromethylpyrrol-3-yl)-4-fluorophenoxy acetate (compound Nr. 4)

Ethyl bromoacetate (0.22 g; 1.3 mmoles) are added to a mixture of 3-(4-chloro-2-fluoro-5-hydroxyphenyl)-2,4-dibromo-1-methyl-5-trifluoromethylpyrrole (0.55 g; 1.2 mmoles) and potassium carbonate (0.17 g; 1.26 mmoles) in DMF (4 ml). The mixture is heated to 50 ° C. for 4 hours. The reaction mixture is poured into water (10 ml), extracted with ethyl ether (3×20 ml), the ether phase is washed with a saturated solution of sodium chloride, anhydrified on sodium sulfate and concentrated in a rotavapor. The raw product obtained (0.65 g) is chromatographed on silica gel, eluating with n-hexane/ethyl acetate 85:15. 0.38 g of product are obtained in the form of a colourless oil.

$^1$H-NMR (CDCl$_3$): δ at 1.29 (t,3H, CH$_3$); 3.78 (bs, 3H, NCH$_3$); 4.26 (q, 2H, OCH$_2$); 4.69 (s, 2H, OCH$_2$CO); 6.77 (d, 1H, aromatic); 7.25 (d, 1H, aromatic).

$^{19}$F-NMR (CDCl$_3$): δ at −118.9 (m, 1F, aromatic); −57.0 (s, 3F, CF$_3$).

EXAMPLE 5

Operating analogously to the procedure described in example 4, the following compounds were prepared starting from 3-(4-chloro-2-fluoro-5-hydroxyphenyl)-2,4-dibromo-1-methyl-5-trifluoromethylpyrrole and from the corresponding halides or mesylates:

3-[4- chloro -2-fluoro-5-(2-propinyloxy)phenyl]-2,4-dibromo-1-methyl-5-trifluoromethylpyrrole having a melting point at 83° C. (Compound Nr. 5)
$^1$H-NMR (CDCl$_3$): δ at 2.53 (t, 1H, C≡CH); 3.8 (bs, 3H, NCH$_3$); 4.77 (m, 2H, OCH$_2$); 6.91 (d, 1H, aromatic); 7.24 (d, 1H, aromatic).
$^{19}$F-NMR (CDCl$_3$): δ at −119.2 (t, 1F, aromatic); −57.1 (s, 3F, CF$_3$).

Operating analogously to the procedure described in example 4, the following compounds were prepared starting from 2-bromo-3-(4-chloro-2-fluoro-5-hydroxyphenyl)-1-methyl-5-tri-fluoromethylpyrrole and from the corresponding halides or mesylates:

ethyl [5-(2-bromo-1-methyl-5-trifluoromethyl pyrrol-3-yl)-2-chloro-4-fluorophenoxy]acetate (Compound Nr. 6)
$^1$H-NMR (CDCl$_3$): δ at 1.30 (t,3H, CH$_3$); 3.75 (bs, 3H, NCH$_3$); 4.27 (q, 2H, OCH$_2$); 4.69 (s, 2H, OCH$_2$CO); 6.77 (bs, 1H, pyrrole); 7.01 (d, 1H, aromatic); 7.21 (d, 1H, aromatic).
$^{19}$F-NMR (CDCl$_3$): δ at −121.5 (t, 1F, aromatic); −60.3 (s, 3F, CF$_3$).

2-bromo-3-[4-chloro-2-fluoro-5-(2-propinyloxy) phenyl]-1-methyl-5-trifluoromethylpyrrole having a melting point at 93° C. (Compound Nr. 7)
$^1$H-NMR (CDCl$_3$): δ at 2.56 (t, 1H, C≡CH); 3.76 (bs, 3H, NCH$_3$); 4.77 (m, 2H, OCH$_2$); 6.78 (bs, 1H, pyrrole); 7.19 (d, 1H, aromatic); 7.23 (bs, 1H, aromatic).
$^9$F-NMR (CDCl$_3$): δ at −121.7 (t, 1F, aromatic); −60.3 (s, 3F, CF$_3$).

EXAMPLE 6

Preparation of methyl 2-chloro-5- (2,4-dibromo-1-methyl-5-trifluoromethylpyrrol-3-yl)-4-fluorobenzoate (Compound Nr. 8)

A solution of bromine (1.28 g; 8.04 mmoles) in dioxane (10 ml) are dripped into a solution of methyl 2-chloro-5-(1-methyl-5-trifluoromethylpyrrol-3-yl)-4-fluorobenzoate (0.9 g; 2.68 mmoles) in dioxane (5 ml). The mixture is maintained under stirring at room temperature for 2 hours and is then heated to 80° C. for 2 hours. After evaporation of the solvent in a rotavapor, ethyl ether (50 ml) is added to the residue which is washed with a saturated solution of sodium metabisulfite (20 ml) and then with water, anhydrified with sodium sulfate and concentrated in a rotavapor. The raw product obtained (0.7 g) is chromatographed on silica gel, eluating with n-hexane/ethyl acetate 85:15. 0.25 g of solid white product are obtained with a melting point of 97° C.
$^1$H-NMR (CDCl$_3$): δ at 3.80 (bs, 3H, NCH$_3$) ; 3.93 (s, 3H, CO$_2$CH$_3$) ; 7.31 (d, 1H, aromatic); 7.90 (d, 1H, aromatic)
$^{19}$F-NMR (CDCl$_3$): δ at −104.5 (m, 1F, aromatic); −57.1 (s, F, CF$_3$).

EXAMPLE 7

Preparation of 1-methylethyl 2-chloro-5-(2,4-dibromo-1-methyl-5-trifluoromethylpyrrol-$^3$-yl)-4-fluorobenzoate (Compound Nr. 9)

Isopropanol (0.2 g; 3.2 mmoles), 1,5-diazabicyclo -[4.3.0] non-5-ene (0.21 g; 1.6 mmoles) are added to a mixture of 2-chloro-5-(2,4-dibromo-1-methyl-5-trifluoromethylpyrrol-3-yl)-4-fluorobenzoic acid (0.8 g; 1.6 mmoles) and N,N'-carbonyldiimidazole (0.77 g; 1.6 mmoles) in DMF (4 ml) heated to 40° C. for 1.5 hours, and the mixture is heated to 40° C. for 2 hours. The reaction mixture is poured into water (10 ml), extracted with ethyl ether (3×20 ml), the ether phase is washed with a saturated solution of sodium chloride, anhydrified on sodium sulfate and concentrated in a rotavapor. The raw product obtained (0.8 g) is chromatographed on silica gel, eluating with n-hexane/ethyl acetate 90:10. 0.4 g of product are obtained in the form of a colourless oil.
$^1$H-NMR (CDCl$_3$): δ at 2.76 (d, 6H, CH$_3$); 3.80 (bs, 3H, NCH$_3$); 5.28 (q, 1H, OCH); 7.29 (d, 1H, aromatic); 7.82 (d, 1H, aromatic).
$^{19}$F-NMR (CDCl$_3$): δ at −105.2 (m, 1F, aromatic); −57.1 (s, 3F, CF$_3$).

EXAMPLE 8

Operating analogously to the procedure described in example 7, the following compounds were prepared starting from 2-chloro-5-(2,4-dibromo-1-methyl-5-trifluoromethylpyrrol-3-yl)-4-fluorobenzoic acid and from the corresponding alcohols or amines:

ethyl 2-chloro-5-(2,4-dibromo-1-methyl-5-trifluoromethylpyrrol-3-yl)-4-fluorobenzoate (Compound Nr. 10)
$^1$H-NMR (CDCl$_3$): δ at 1.40 (t, 3H, CH$_3$) ; 3.79 (bs, 3H, NCH$_3$); 4.40 (q, 2H, OCH$_2$); 7.30 (d, 1H, aromatic); 7.87 (d, 1H, aromatic).
$^{19}$F-NMR (CDCl$_3$): δ at −104.9 (t, 1F, aromatic); −57.1 (s, 3F, CF$_3$).

N,N-dimethyl 2-chloro-5-(2,4-dibromo-1-methyl-5-trifluoromethylpyrrol-3-yl)-4 - fluorobenzamide (Compound Nr. 11)
$^1$H-NMR (CDCl$_3$): δ at 2.39 (s, 3H, CH$_3$); 3.14 (s, 3H, CH$_3$); 3.79 (bs, 3H, NCH$_3$ pyrrole); 7.23 (d, 1H, aromatic); 7.28 (d, 1H, aromatic).
$^{19}$F-NMR (CDCl$_3$): δ at −108.8 (bs, 1F, aromatic); −57.1 (s, 3F, CF$_3$).

1-[2-chloro-5-(2.4-dibromo-1-methyl-5-trifluoromethylpyrrol-3-yl)-4-fluorobenzoyl] pyrrolidine (Compound Nr. 12)
$^1$H-NMR (CDCl$_3$): δ at 1.96 (m, 4H, CH$_2$); 3.27 (m, 2H, NCH$_2$ ); 3.67 (m, 2H, NCH$_2$ ); 3.78 (bs, 3H, NCH$_3$); 7.23 (d, 1H, aromatic); 7.28 (d, 1H, aromatic).
$^{19}$F-NMR (CDCl$_3$): δ at −108.8 (bs, 1F, aromatic); −57.1 (s, 3F, CF$_3$).

EXAMPLE 9

Preparation of 3-(4-chloro-2-fluoro-5-hydroxyphenyl)-2,4-dichloro-1-methyl-5-trifluoromethylpyrrole (Compound Nr. 13).

N-chlorosuccinimide (1.66 g; 12.4 mmoles) is added to a solution of 4-(4-chloro-2-fluoro-5-acetoxyphenyl)-1-methyl-2-trifluoromethylpyrrole (1.9 g; 5.7 mmoles) in dimethylformamide (30 ml) and the mixture is heated to 100° C. for 1.5 hours. The reaction mixture is diluted with water (10 ml), extracted with ethyl ether (50 ml), the organic phase is washed with a saturated solution of sodium chloride, anhydrified with sodium sulfate and concentrated in a rotavapor. The reaction raw product (2.3 g) dissolved in a mixture of methanol/water 2:1 (45 ml) is treated with potassium carbonate (1.2 g). The mixture is maintained under stirring at room temperature for 17 hours. The reaction mixture is diluted with ethyl ether (100 ml), the ether phase is washed with a solution of hydrochloric acid at 5%, and is then washed until neutral pH with a saturated solution of sodium chloride, it is then anhydrified with sodium sulfate and concentrated in a rotavapor. 1.9 g of product are obtained. GC-MS: m/e 361

EXAMPLE 10

Preparation of 3-[4-chloro-2-fluoro-5-(2-propinyloxy)phenyl]-2,4-dichloro-1-methyl-5-trifluoromethyl pyrrole (Compound Nr. 14).

2-propinyl methanesulfonate (0.35 g; 2.6 mmoles) is added to a mixture of 3-(4-chloro-2-fluoro-5-hydroxyphenyl) -2,4-dichloro-1-methyl-5-trifluoromethyl pyrrole (0.9 g; 2.5 mmoles) and potassium carbonate (0.33 g; 2.39 mmoles) in methylisobutylketone (10 ml). The mixture is heated to 80° C. for 3 hours. The reaction mixture is poured into water (10 ml), extracted with ethyl ether (3×20 ml), the ether phase is washed with a saturated solution of sodium chloride, anhydrified with sodium sulfate and concentrated in a rotavapor. The raw product obtained (1.0 g) is chromatographed on silica gel, eluating with n-hexane/ethyl acetate 90:10. 0.40 g of solid white product are obtained.

$^1$H-NMR (CDCl$_3$) : δ at 2.55 (t, 1H, C≡CH); 3.75 (bs, 3H, NCH$_3$); 4.76 (m, 2H, OCH$_2$); 7.05 (d, 1H, aromatic); 7.25 (d, 1H, aromatic).

$^{19}$F-NMR (CDCl$_3$): δ at −119.6 (m, 1F, aromatic); −57.2 (s, 3F, CF$_3$).

EXAMPLE 11

Operating analogously to the procedure described in example 10, the following compounds were prepared starting from 3-(4-chloro-2-fluoro-5-hydroxyphenyl)-2,4-dichloro-1-methyl-5-trifluoromethylpyrrole and from the corresponding halides or mesylates:

ethyl [2-chloro-5-(2,4-dichloro-1-methyl-5-trifluoromethylpyrrol-3-yl)-4-fluorophenoxy]acetate (Compound Nr. 15).
$^1$H-NMR (CDCl$_3$) δ at 1.28 (t, 3H, CH$_3$); 3.74 (bs, 3H, NCH$_3$) 4.26 (q, 2H, OCH$_2$); 4.69 (s, 2H, OCH$_2$CO); 6.82 (d, 1H, aromatic); 7.26 (d, 1H, aromatic). 19F-NMR (CDCl$_3$): δ at −119.3 (m, 1F, aromatic); −57.2 (s, 3F, CF$_3$).

EXAMPLE 12

Preparation of 4-bromo3-(4-chloro-2-fluoro-5-hydroxyphenyl)-2-chloro-1-methyl-5-trifluoromethylpyrrole (Compound Nr. 16).

A solution of SO$_2$Cl$_2$ (0.39 g; 2.88 mmole) in ethyl ether (10 ml) are dripped into a solution of 3-(4-chloro-2-fluoro-5-hydroxyphenyl)-2,4-dibromo-1-methyl-5-trifluoromethyl pyrrole (1.3 g; 2.88 mmoles) in ethyl ether (10 ml), at 0° C. After 30 minutes at 0° C. the reaction mixture is diluted with additional ethyl ether (30 ml) and washed with water, followed by a solution at 5% of NaHCO$_3$ and finally with s saturated solution of sodium chloride; it is then anhydrified with sodium sulfate and concentrated in a rotavapor. 1.1 g of product are obtained. GC-MS: m/e 405

EXAMPLE 13

Preparation of 4-bromo-3-[4-chloro-2-fluoro-5-(2-propinyl oxy)phenyl]-2-chloro-1-methyl-5-trifluoromethyl pyrrole (Compound Nr. 17).

2 propinyl methanesulfonate (0.22 g; 1.61 mmoles) is added to a mixture of 4-bromo-3-(4-chloro-2-fluoro-5-hydroxyphenyl)-2-chloro-1-methyl-5-trifluoromethyl pyrrole (0.6 g; 1.47 mmoles) and potassium carbonate (0.21 g; 1.54 mmoles) in methylisobutylketone (6 ml). The mixture is heated to 80° C. for 3 hours. The reaction mixture is poured into water (10 ml), extracted with ethyl ether (3×20 ml), the ether phase is washed with a saturated solution of sodium chloride, anhydrified with sodium sulfate and concentrated in a rotavapor. The raw product obtained (0.65 g) is chromatographed on silica gel, eluating with n-hexane/ethyl acetate 85:15. 0.28 g of solid white product with a melting point of 87° C., are obtained.

$^1$H-NMR (CDCl$_3$): δ at 2.51 (t, 1H, C≡CH); 3.76 (bs, 3H, NCH$_3$); 4.77 (m, 2H, OCH$_2$); 7.03 (d, 1H, aromatic); 7.25 (d, 1H, aromatic).

$^{19}$F-NMR (CDCl$_3$): δ at −119.6 (m, 1F, aromatic); −57.1 (s, 3F, CF$_3$).

EXAMPLE 14

Operating analogously to the procedure described in example 13, the following compounds were prepared starting from 4-bromo-3-(4-chloro-2-fluoro-5-hydroxyphenyl)-2-chloro-1-methyl-5-trifluoromethylpyrrole and from the corresponding halides or mesylates:

ethyl-5-(4-bromo-2-chloro-1-methyl-5-trifluoromethyl pyrrol-3-yl)-2-chloro-4-fluorophenoxyacetate (Compound Nr.18).
$^1$H-NMR (CDCl$_3$): δ at 1.28 (t,3H, CH$_3$); 3.75 (bs, 3H, NCH$_3$); 4.26 (q, 2H, OCH$_2$); 4.69 (s, 2H, OCH$_2$CO); 6.81 (d, 1H, aromatic); 7.25 (d, 1H, aromatic).
$^{19}$F-NMR (CDCl$_3$): δ at −119.2 (m, 1F, aromatic); −57.0 (s, 3F, CF$_3$).

EXAMPLE 15

Operating analogously to the procedures described in Examples 1–14, the following compounds were further synthesized ($^1$H and $^{19}$FNMR spectra, and elemental analyses in agreement with the expected values):

methyl[2-chloro-5-(2,4-dichloro-1-methyl-5-trifluoromethylpyrrol-3-yl)-4-fluorophenyoxy]acetate (Compound Nr. 19)

methyl [2-chloro-5-(2,4-dichloro-1-methyl-5-trifluoromethylpyrrol-3-yl)-4-fluoro]cinnamate (Compound Nr. 20)

N,N-dimethyl-[2-chloro-5-(2,4-dichloro-1-methyl-5-trifluoromethylpyrrol-3-yl)-4-fluorophenyloxy]acetamide (compound Nr. 21)

methyl (RS)-2-chloro-3-[2-chloro-5-(2,4-dichloro-1-methyl-5-trifluoromethylpyrrol-3-yl)-4-fluorophenyl]propionate (Compound Nr. 22)

2-methoxyethyl[2-chloro-5-(2,4-dichloro-1-methyl-5-trifluoromethylpyrrol-3-yl)-4-fluorophenoxy]acetate (Compound 23)

2-methoxyethyl[2-chloro-5-(2,4-dibromo-1-methyl-5-trifluoromethylpyrrol-3-yl)-4-fluorophenoxy]acetate (Compound Nr. 24)

3-(4-chloro-5-cyanomethoxy-2-fluorophenyl)-2,4-dichloro-1-methyl-5-trifluoromethylpyrrole (Compound Nr. 25)

3-[4-chloro-2-fluoro-5-(4-methoxy-2-butynyloxy) phenyl]-2,4-dichloro-1-methyl-5-trifluoromethylpyrrole (Compound Nr. 26)

3-(5-acetylmethoxy-4-chloro-2-fluorophenyl)-2,4-dichloro-1-methyl-5-trifluoromethylpyrrole (Compound Nr. 27)

3-[4-chloro-2-fluoro-5-(2,2,2-trifluoroethoxy)phenyl]-2,4-dichloro-1-methyl-5-trifluoromethylpyrrole (Compound Nr. 28)

3-[4-chloro-2-fluoro-5-(2-methoxyiminopropoxy)phenyl]-2,4-dichloro-1-methyl-5-trifluoromethylpyrrole (Compound Nr. 29)

3-[4-chloro-2-fluoro-5-(2-propynylthio)phenyl]-2,4-dichloro-1-methyl-5-trifluoromethylpyrrole (Compound Nr. 30)

3-[4-chloro-2-fluoro-5-(2-methoxyiminoethoxy)phenyl]-2,4-dichloro-1-methyl-5-trifluoromethylpyrrole (Compound Nr. 31)

3-[4-chloro-2-fluoro-5-(1,3-dioxolan-2-ylmethoxy)phenyl]-2,4-dichloro-1-methyl-5-trifluoromethylpyrrole (Compound Nr. 32)

3-[4-chloro-2-fluoro-5-(5-trifluoromethyl-1,3,4-thiadiazol-2-yloxy)-phenyl]-2,4-dichloro-1-methyl-5-trifluoromethylpyrrole (Compound Nr. 33)

3-[4-chloro-2-fluoro-5-(5-methyl-1,3,4-thiadiazol-2-yloxy)-phenyl]-2,4-dichloro-1-methyl-5-trifluoromethylpyrrole (Compound Nr. 34)

3-[4-chloro-2-fluoro-5-(5-ethyl-1,3,4-thiadiazol-2-yloxy)-phenyl]-2,4-dichloro-1-methyl-5-trifluoromethylpyrrole (Compound Nr. 35)

3-[4-chloro-2-fluoro-5-(pyrid-3-yloxy)-phenyl]-2,4-dichloro-1-methyl-5-trifluoro-methyl-pyrrole (Compound Nr.36)

3-[4-chloro-2-fluoro-5-(2-methylthiadiazol-4-ylmethoxy)phenyl]-2,4-dichloro-1-methyl-5-trifluoro-methyl-pyrrole (Compound Nr. 37)

3-[4-chloro-2-fluoro-5-(3-ethoxycarbonyl-isoxazol-5-ylmethoxy)phenyl]-2,4-dichloro-1-methyl-5-trifluoro-methyl-pyrrole (Compound Nr. 38)

3-[4-chloro-2-fluoro-5-(5-methoxycarbonylfuran-2-ylmethoxy)phenyl]-2,4-dichloro-1-methyl-5-trifluoro-methylpyrrole (Compound Nr. 39)

methyl 4-[2-chloro-5-(2,4-dichloro-1-methyl-5-trifluoromethylpyrrol-3-yl)-4-fluorophenoxy]-3-methoxybut-(E)-2-enoate (Compound Nr. 40)

3-(4-chloro-5-cyclopropylmethoxy-2-fluorophenyl)-2,4-dichloro-1-methyl-5-trifluoromethylpyrrole (Compound Nr. 41)

3-(4-chloro-2-fluoro-5-isopropoxyphenyl)-2,4-dichloro-1-methyl-5-trifluoromethylpyrrole (Compound Nr. 42)

3-(4-chloro-5-cyclopentoxy-2-fluorophenyl)-2,4-dichloro-1-methyl-5-trifluoromethylpyrrole (Compound Nr. 43)

ethyl [2-chloro-5-(2,4-dichloro-1-methyl-5-trifluoromethylpyrrol-3-yl)-4-fluorophenoxy]pyruvate (Compound Nr. 44)

methyl [2-chloro-5-(2,4-dichloro-1-methyl-s-trifluoromethylpyrrol-3-yl)-4-fluorophenoxy]pyruvate (Compound Nr. 45)

ethyl 4-[2-chloro-5- (2,4-dichloro-1-methyl-5-trifluoromethylpyrrol-3-yl)-4-fluorophenoxy]crotonate (Compound Nr. 46)

methyl 2-[2-chloro-5-(2,4-dichloro-1-methyl-5-trifluoromethylpyrrol-3-yl)-4-fluorophenoxy]benzoate (Compound Nr. 47)

methyl [2-chloro-5-(2,4-dichloro-1-methyl-5-pentafluoroethylpyrrol-3-yl)-4-fluorophenoxy]acetate (Compound Nr. 48)

ethyl [2-chloro-5-(2,4-dichloro-1-methyl-5-pentafluoroethylpyrrol-3-yl)-4-fluorophenoxy]acetate (Compound Nr. 49)

3-[4-chloro-2-fluoro-5-(3-butyn-2-yloxy)phenyl]-2,4-dichloro-1-methyl-5-trifluoro-methylpyrrole (Compound Nr. 50)

3-[4-chloro-2-fluoro-5-(2-propynyloxy)phenyl]-2,4-dichloro-1-methyl-5-pentafluoroethylpyrrole (Compound Nr. 51)

ethyl[2-chloro-5-(2,4-dichloro-1-methyl-5-trifluoromethylpyrrol-3-yl)phenoxy]acetate (Compound Nr. 52)

5-chlorodifluoromethyl-3-[4-chloro-2-fluoro-5-(2-propynyloxy)phenyl]-2,4-dichloro-1-methylpyrrole (Compound Nr. 53)

ethyl[2-chloro-5-(5-chlorodifluoromethyl-2,4-dichloro-1-methylpyrrol-3-yl)-4-fluorophenoxy]acetate (Compound Nr. 54)

3-[4-chloro-2-fluoro-5-(2-propynyloxy)phenyl]-2,4-dichloro-1-ethyl-5-trifluoromethylpyrrole (Compound Nr. 55)

ethyl [2-chloro-5-(-2,4-dichloro-1-ethyl-5-trifluoromethylpyrrol-3-yl)-4-fluorophenoxy]acetate (Compound Nr. 56)

3-[4-chloro-2-fluoro-5-(2-propynyloxy)phenyl]-2,4-dichloro-1,5-dimethylpyrrole (Compound Nr. 57)

ethyl [2-bromo-5-(-2,4-dichloro-1-methyl-5-trifluoromethylpyrrol-3-yl)-phenoxy]acetate (Compound Nr. 58)

3-[4-chloro-2-fluoro-5-(2-propynyloxy)phenyl]-2,4-dichloro-1-methoxy-5-trifluoromethylpyrrole (Compound Nr. 59)

ethyl[2-chloro-5-(2,4-dichloro-1-methoxy-5-trifluoromethylpyrrol-3-yl)-4-fluorophenoxy]acetate (Compound Nr. 60)

EXAMPLE 16
Determination of the Herbicidal Activity

The herbicidal activity of the compounds of the invention was evaluated with respect to both monocotyledon and dicotyledon weeds, in post- and pre-emergence treatment.

The evaluation tests were carried out according to the following operative procedures.

Vases (diameter over 10 cm, height 10 cm) containing sandy medium were prepared. One of the following weeds was planted in each of them: *Abutilon theofrasti* (AT), *Amarantus retraflexus* (AR), *Chenopodium album* (CA), *Convolvulus sepium* (CS), *Portulaca oleracea* (PO), *Solanum nigrum* (SN), *Ipomea purpurea* (IP).

Water was added to each vase in a suitable quantity for a good germination of the seeds. The vases were divided into two groups, each group containing at least 5 vases for each weed.

The first group was not treated with herbicide and was used as a comparison (blank).

The second group of vases was treated fifteen days after sowing (i.e. when the small weed plants, depending on the species, were 10–15 cm high) with a hydroacetone dispersion at 20% by volume of acetone of the product to be evaluated (herbicidal activity in post-emergence). All the vases were kept under observation in a conditioned environment under the following environmental conditions:

temperature: 15–26° C.

relative humidity: 60% photoperiod: 16 hours light intensity: 10000 lux

Every two days, the vases were uniformly watered to ensure a sufficient degree of humidity for a good development of the plants.

21 days after treatment, the herbicidal activity was evaluated on the basis of the following scale of values referring to the percentage of damage measured on the treated plants with respect to those not treated (blank):

0=0–20% of damage
1=21–40%
2=41–60%
3=61–80%
4=81–95%
5=death of the plant treated.

The results obtained are indicated in Table 1 below:

TABLE 1

| Herbicidal activity in post-emerqence at doses of 150 g/hectare | | | | | | | |
|---|---|---|---|---|---|---|---|
| | WEED | | | | | | |
| COMPOUND | AT | AR | CA | CS | PO | SN | IP |
| 4 | 5 | 5 | 5 | 5 | 5 | 5 | 5 |
| 5 | 5 | 5 | 5 | 5 | 5 | 5 | 5 |
| 14 | 5 | 5 | 5 | 5 | 5 | 5 | 5 |
| 15 | 5 | 5 | 5 | 5 | 5 | 5 | 5 |
| 17 | 5 | 5 | 5 | 5 | 5 | 5 | 5 |
| 18 | 5 | 5 | 5 | 5 | 5 | 5 | 5 |

What is claimed is:

1. A pyrrolic compound having the formula (I)

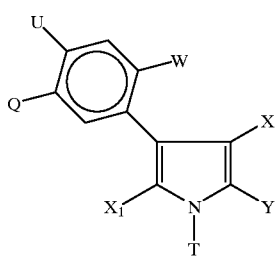

wherein:
W represents a hydrogen, fluorine or chlorine atom;
U represents a halogen atom, an alkyl, haloalkyl group, a cyano group, a nitro group;
Q represents a hydrogen atom, a halogen atom, a $C_1$–$C_8$ alkyl group, a $C_1$–$C_8$ halogenalkyl group, a $C_3$–$C_6$ cycloalkyl group, a $C_4$–$C_8$ cycloalkylalkyl group, an alkenyl group, said groups being unsubstituted or further substituted by one or more substituents selected from halogen atoms, $C_1$–$C_4$ alkoxyl groups, $C_1$–$C_4$ haloalkoxyl groups, $C_1$–$C_4$ alkylthio groups, $C_1$–$C_4$ haloalkylthio groups, $C_1$–$C_4$ alkylsulfinic groups, $C_1$–$C_4$ haloalkylsulfinic groups, $C_1$–$C_4$ alkylsulfonic groups, haloalkylsulfonic groups;
or it represents a ZR, $COR_1$, $CO_2R_2$, $CH_2CHR_3CO_2R_2$, $CH=CHR_3CO_2R_2$, $CR_4=NOR_5$, $CO-NR_6R_7$, $CN$, $NO_2$, $NR_8R_9$, $NR_{10}SO_2R_{11}$, $N(SO_2R_{11})_2$, $NR_{12}-CO-R_{13}$, $NR_{14}-CO-OR_{15}$, $NR_{16}-CO-NR_{17}R_{18}$ group;
Groups U and Q when joined to each other by means of saturated carbon atoms or unsaturated carbon atoms, or $C=Z_1$ groups, or oxygen atoms, or $S(O)_m$ groups, or $NR_{19}$ groups to form a cyclic ring having up to 9 members, in which the carbon atoms are unsubstituted or substituted with one or more $C_1$–$C_4$ alkyl or haloalkyl groups;

T represents a hydrogen atom, a $C_1$–$C_8$ alkyl or haloalkyl group, a $C_1$–$C_8$ alkoxyalkyl or haloalkoxyalkyl group, a $Z_2R_{11}$ group;
X represents a hydrogen atom, a halogen atom, a $C_1$–$C_8$ halogenalkyl group, a $CO_2R_{21}$ group, a $CO-NR_6R_7$ group;
$X_1$ represents a hydrogen atom, a halogen atom, a $C_1$–$C_8$ halogenalkyl group, a $CO_2R_{22}$ group, a $CO-NR_6R_7$ group;
Y represents a $C_1$–$C_8$ alkyl or haloalkyl group, a $Z_3Y_1$ group;
$Y_1$ represents a $C_1$–$C_8$ alkyl or haloalkyl group;
$Z_1$, $Z_2$, $Z_3$ represent O or S(O)n wherein n=0–1;
$Z_1$ represents O or S
m=0–2
R represents a hydrogen atom, a $C_1$–$C_8$ alkyl group, a $C_3$–$C_6$ cycloalkyl group, a $C_4$–$C_8$ cycloalkylalkyl group, a $C_2$–$C_8$ alkenyl group, a $C_2$–$C_8$ alkynyl group, an aryl group, an arylalkyl group, a heterocyclic group with 5 or δ atoms containing from 1 to 4 heteroatoms, the same or different, selected from N, O, S, a heterocyclylalkyl group; said groups are unsubstituted or further substituted by one or more substituents selected from halogen atoms, $C_1$–$C_4$ alkoxyl groups, $C_1$–$C_4$ haloalkoxyl groups, $C_1$–$C_4$ alkylthio groups, $C_1$–$C_4$ haloalkylthio groups, $C_1$–$C_4$ alkylsulfinic groups, $C_1$–$C_4$ haloalkylsulfinic groups, $C_1$–$C_4$ alkylsulfonic groups, $C_1$–$C_4$ haloalkylsulfonic groups, COOH groups, $C_2$–$C_6$ alkoxycarbonyl groups, $C_2$–$C_6$ haloalkoxycarbonyl groups, $C_3$–$C_8$ alkoxycarbonylcarbonyl groups, $C_3$–$C_8$ haloalkoxycarbonylcarbonyl groups, $C_2$–$C_6$ alkylaminocarbonyl groups, $C_3$–$C_9$ dialkylaminocarbonyl groups, $C_3$–$C_7$ alkylaminocarbonylcarbonyl groups, $C_4$–$C_{10}$ dialkylaminocarbonylcarbonyl groups, $C_2$–$C_6$ alkylcarbonyl groups, $C_2$–$C_6$ aloxyalkylcarbonyl groups, $C_4$–$C_8$ alkoxyiminoalkyl groups, $C_4$–$C_8$ akoxyiminohaloalkyl groups, CHO groups, CN groups, $NO_2$ groups;
$R_1$, $R_2$, $R_4$, $R_5$, $R_{10}$, $R_{11}$, $R_{12}$, $R_{13}$, $R_{14}$, $R_{15}$, $R_{16}$, $R_{19}$, $R_{20}$, $R_{21}$, $R_{22}$, represent a hydrogen atom, or a $C_1$–$C_6$ alkyl or haloalkyl group, a $C_3$–$C_6$ cycloalkyl group, a $C_7$–$C_{12}$ arylalkyl group or an aryl group, said arylalkyl and aryl groups also unsubstituted or substituted;
$R_3$ represents a hydrogen atom, a halogen atom, or a $C_1$–$C_2$ alkyl or haloalkyl group;
$R_6$, $R_7$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also unsubstituted or substituted, or they jointly represent a $C_2$–$C_5$ alkylene chain;
$R_8$, $R_9$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also unsubstituted or substituted, or they jointly represent a $C_2$–$C_5$ alkylene chain;
$R_{17}$, $R_{18}$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also unsubstituted or substituted, or they jointly represent a $C_2$–$C_5$ alkylene chain.

2. A process for the preparation of the compound having the formula (I) according to claim 1, comprising reacting an alkyne having a formula (II):

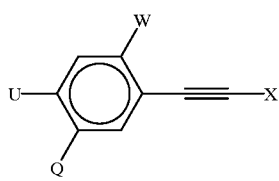

(II)

with an amino acid having a formula (III):

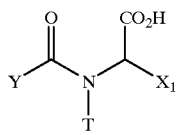

(III)

wherein W, U, Q. Y, T and $X_1$ are defined as in claim 1, in an inert organic solvent and in the presence of a dehydrating agent, at a temperature ranging from 50° C. to the boiling point of the reaction mixture.

3. A herbicidal composition comprising solid carriers, liquid diluents or surface-active agents and at least one of the compounds according to claim 1.

4. A method for controlling weeds in cultivated areas, comprising applying one or more herbicidal composition according to claim 3 said areas.

5. The method according to claim 4, wherein the active compounds are distributed on the ground at doses ranging from 1 to 1000 g per hectare.

6. A compound according to claim 1, wherein said pyrrolic compound is selected from the group consisting of:
   3-(4-chloro-2-fluoro-5-hydroxyphenyl)-2,4-dibromo-1-methyl-5-trifluoromethylpyrrole,
   2-chloro-5-(2,4-dibromo-1-methyl-5-trifluoromethylpyrr-ol-3-yl)-4-fluorophenoxyacetate,
   3-[4-chloro-2-fluoro-5-(2-propinyloxy)phenyl]-2,4-dibromo-1-methyl-5-trifluoromethylpyrrole,
   3-(4-chloro-2-fluoro-5-hydroxyphenyl)-2,4-dichloro-1-methyl-5-trifluoromethylpyrrole,
   3-[4-chloro-2-fluoro-5-(2-propinyloxy)phenyl]-2,4-dichloro-1-methyl-5-trifluoromethylpyrrole,
   ethyl[2-chloro-5-(2,4-dichloro-1-methyl-5-trifluoromethyl-pyrrol-3-yl)-4-fluorophenoxy]acetate,
   4-bromo-3-(4-chloro-2-fluoro-5-hydroxyphenyl)-2-chloro-1-methyl-5-trifluoromethylpyrrole,
   4-bromo-3-[4-chloro-2-fluoro-5-(2-propinyloxy)phenyl]-2-chloro-1-methyl-5-trifluoromethylpyrrole,
   ethyl-5-(4-bromo-2-chloro-1-methyl-5-trifluoromethylpyrrol-3-yl)-2-chloro-4-fluorophenoxyacetate. 18,
   methyl[2-chloro-5-(2,4-dichloro-1-methyl-5-trifluoromethylpyrrol-3-yl)-4-fluorophenyoxy]acetate,
   N,N-dimethyl-[2-chloro-5-(2,4-dichloro-1-methyl-5-trifluoromethylpyrrol-3-yl)-4-fluorophenyloxy]acetamide.21,
   3-(4-chloro-5-cyanomethoxy-2-fluorophenyl)-2,4-dichloro-1-methyl-5-trifluoromethylpyrrole,
   3-(5-acetylmethoxy-4-chloro-2-fluorophenyl)-2,4-dichloro-1-methyl-5-trifluoromethylpyrrole,
   3-[4-chloro-2-fluoro-5-(2-methoxyiminopropoxy) phenyl]-2,4-dichloro-1-methyl-5-trifluoromethylpyrrole,
   ethyl [2-chloro-5-(2,4-dichloro-1-methyl-5-trifluoromethylpyrrol-3-yl)-4-fluorophenoxy]pyruvate,
   methyl [2-chloro-5-(2,4-dichloro-1-methyl-5-pentafluoroethylpyrrol-3-yl)-4-fluorophenoxy]acetate,
   ethyl [2-chloro-5-(2,4-dichloro-1-methyl-5-pentafluoroethylpyrrol-3-yl)-4-fluorophenoxy]acetate,
   3-[4-chloro-2-fluoro-5-(3-butyn-2-yloxy)phenyl]-2,4-dichloro-1-methyl-5-trifluoro-methylpyrrole,
   3-[4-chloro-2-fluoro-5-(2-propynyloxy)phenyl]-2,4-dichloro-1-methyl-5-pentafluoroethylpyrrole,
   3-[4-chloro-2-fluoro-5-(2-propynyloxy)phenyl]-2,4-dichloro-1-ethyl-5-trifluoromethylpyrrole, and
   ethyl [2-chloro-5-(-2,4-dichloro-1-ethyl-5–5-trifluoromethylpyrrol-3-yl)-4-fluorophenoxy] acetate.

7. A method for controlling weeds in cultivated areas, comprising applying to said areas a herbicidal composition comprising one or more pyrrolic compound having the formula (I)

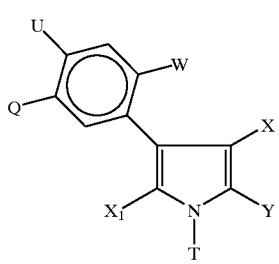

(I)

wherein:
   W represents a hydrogen, fluorine or chlorine atom;
   U represents a halogen atom, an alkyl, haloalkyl group, a cyano group, a nitro group;
   Q represents a hydrogen atom, a halogen atom, a $C_1$–$C_8$ alkyl group, a $C_1$–$C_8$ halogenalkyl group, a $C_3$–$C_6$ cycloalkyl group, a $C_4$–$C_8$ cycloalkylalkyl group, an alkenyl group, said groups are unsubstituted or further substituted by one or more substituents selected from halogen atoms, $C_1$–$C_4$ alkoxyl groups, $C_1$–$C_4$ haloalkoxyl groups, $C_1$–$C_4$ alkylthio groups, $C_1$–$C_4$ haloalkylthio groups, $C_1$–$C_4$ alkylsulfinic groups, $C_1$–$C_4$ haloalkylsulfinic groups, $C_1$–$C_4$ alkylsulfonic groups, haloalkylsulfonic groups;
   or it represents a ZR, $COR_1$, $CO_2R_2$, $CH_2CHR_3CO_2R_2$, $CH=CHR_3CO_2R_2$, $CR_4=NOR_5$, $CO-NR_6R_7$, CN, $NO_2$, $NR_8R_9$, $NR_{10}SO_2R_{11}$, $N(SO_2R_{11})_2$, $NR_{12}-CO-R_{13}$, $NR_{14}-CO-OR_{15}$, $NR_{16}-CO-NR_{17}R_{18}$ group;
   Groups U and Q when joined to each other by means of saturated carbon atoms or unsaturated carbon atoms, or $C=Z_1$ groups, or oxygen atoms, or $S(O)_m$ groups, or $NR_{19}$ groups to form a cyclic ring having up to 9 members, in which the carbon atoms are unsubstituted or substituted with one or more $C_1$–$C_4$ alkyl or haloalkyl groups;
   T represents a hydrogen atom, a $C_1$–$C_8$ alkyl or haloalkyl group, a $C_1$–$C_8$ alkoxyalkyl or haloalkoxyalkyl group, a $Z_2R_{11}$ group;
   X represents a hydrogen atom, a halogen atom, a $C_1$–$C_8$ halogenalkyl group, a $CO_2R_{21}$, group, a $CO-NR_6R_7$ group;
   $X_1$ represents a hydrogen atom, a halogen atom, a $C_1$–$C_8$ halogenalkyl group, a cyano group, a $CO_2R_{22}$ group, a $CO-NR_6R_7$ group;

Y represents a $C_1$–$C_8$ alkyl or haloalkyl group, a cyano group, a $Z_3Y_1$ group;

$Y_1$ represents a $C_1$–$C_6$ alkyl or haloalkyl group;

$Z_1$, $Z_2$, $Z_3$ represent O or S(O)n wherein n=0–1;

$Z_1$ represents O or S m=0–2

R represents a hydrogen atom, a $C_1$–$C_8$ alkyl group, a $C_3$–$C_6$ cycloalkyl group, a $C_4$–$C_8$ cycloalkylalkyl group, a $C_2$–$C_8$ alkenyl group, a $C_2$–$C_8$ alkynyl group, an aryl group, an arylalkyl group, a heterocyclic group with 5 or 6 atoms containing from 1 to 4 heteroatoms, the same or different, selected from N, O, S, a heterocyclylalkyl group; said groups are unsubstituted or further substituted by one or more substituents selected from halogen atoms, $C_1$–$C_4$ alkoxyl groups, $C_1$–$C_4$ haloalkoxyl groups, $C_1$–$C_4$ alkylthio groups, $C_1$–$C_4$ haloalkylthio groups, $C_1$–$C_4$ alkylsulfinic groups, $C_1$–$C_4$ haloalkylsulfinic groups, $C_1$–$C_4$ alkylsulfonic groups, $C_1$–$C_4$ haloalkylsulfonic groups, COOH groups, $C_2$–$C_6$ alkoxycarbonyl groups, $C_2$–$C_6$ haloalkoxycarbonyl groups, $C_3$–$C_8$ alkoxycarbonylcarbonyl groups, $C_3$–$C_8$ haloalkoxycarbonylcarbonyl groups, $C_2$–$C_6$ alkylaminocarbonyl groups, $C_3$–$C_9$ dialkylaminocarbonyl groups, $C_3$–$C_7$ alkylaminocarbonylcarbonyl groups, $C_4$–$C_{10}$ dialkylaminocarbonylcarbonyl groups, $C_2$–$C_6$ alkylcarbonyl groups, $C_2$–$C_6$ aloxyalkylcarbonyl groups, $C_4$–$C_8$ alkoxyiminoalkyl groups, $C_4$–$C_8$ akoxyiminohaloalkyl groups, CHO groups, CN groups, $NO_2$ groups;

$R_1$, $R_2$, $R_4$, $R_5$, $R_{10}$, $R_{11}$, $R_{12}$, $R_{13}$, $R_{14}$, $R_{15}$, $R_{16}$, $R_{19}$, $R_{20}$, $R_{21}$, $R_{22}$, represent a hydrogen atom, or a $C_1$–$C_6$ alkyl or haloalkyl group, a $C_3$–$C_6$ cycloalkyl group, a $C_7$–$C_{12}$ arylalkyl group or an aryl group, said arylalkyl and aryl groups also unsubstituted or substituted;

$R_3$ represents a hydrogen atom, a halogen atom, or a $C_1$–$C_2$ alkyl or haloalkyl group;

$R_6$, $R_7$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also unsubstituted or substituted, or they jointly represent a $C_2$–$C_5$ alkylene chain;

$R_8$, $R_9$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also unsubstituted or substituted, or they jointly represent a $C_2$–$C_5$ alkylene chain;

$R_{17}$, $R_{18}$ represent a hydrogen atom, or a $C_1$–$C_6$ alkyl group, a $C_3$–$C_6$ cycloalkyl group, a $C_7$–$C_{12}$ arylalkyl group or an aryl group, said arylalkyl and aryl groups also unsubstituted or substituted, or they jointly represent a $C_2$–$C_5$ alkylene chain.

8. A method according to claim 7, wherein said one or more pyrrolic compound is selected from the group consisting of:

3-(4-chloro-2-fluoro-5-hydroxyphenyl)-2,4-dibromo-1-methyl-5-trifluoromethylpyrrole, 2-chloro-5-(2,4-dibromo-1-methyl-5-trifluoromethylpyrr-ol-3-yl)-4-fluorophenoxyacetate, 3-[4-chloro-2-fluoro-5-(2-propinyloxy)phenyl]-2,4-dibromo-1-methyl-5-trifluoromethylpyrrole, 3-(4-chloro-2-fluoro-5-hydroxyphenyl)-2,4-dichloro-1-methyl-5-trifluoromethylpyrrole, 3-[4-chloro-2-fluoro-5-(2-propinyloxy)phenyl]-2,4-dichloro-1-methyl-5-trifluoromethylpyrrole, ethyl[2-chloro-5-(2,4-dichloro-1-methyl-5-trifluoromethyl-pyrrol-3-yl)-4-fluorophenoxy]acetate, 4-bromo-3-(4-chloro-2-fluoro-5-hydroxyphenyl)-2-chloro-1-methyl-5-trifluoromethylpyrrole, 4-bromo-3-[4-chloro-2-fluoro-5-(2-propinyloxy)phenyl]-2-chloro-1-methyl-5-trifluoromethylpyrrole, ethyl-5-(4-bromo-2-chloro-1-methyl-5-trifluoromethylpyrrol-3-yl)-2-chloro-4-fluorophenoxyacetate, methyl[2-chloro-5-(2,4-dichloro-1-methyl-5-trifluoromethylpyrrol-3-yl)-4-fluorophenyoxy] acetate, N,N-dimethyl-[2-chloro-5-(2,4-dichloro-1-methyl-5-trifluoromethylpyrrol-3-yl)-4-fluorophenyloxy] acetamide.21, 3-(4-chloro-5-cyanomethoxy-2-fluorophenyl)-2,4-dichloro-1-methyl-5-trifluoromethylpyrrole, 3-(5-acetylmethoxy-4-chloro-2-fluorophenyl)-2,4-dichloro-1-methyl-5-trifluoromethylpyrrole, 3-[4-chloro-2-fluoro-5-(2-methoxyiminopropoxy)phenyl]-2,4-dichloro-1-methyl-5-trifluoromethylpyrrole, ethyl [2-chloro-5-(2,4-dichloro-1-methyl-5-trifluoromethylpyrrol-3-yl)-4-fluorophenoxy]pyruvate, methyl [2-chloro-5-(2,4-dichloro-1-methyl-5-pentafluoroethylpyrrol-3-yl)-4-fluorophenoxy]acetate, ethyl [2-chloro-5-(2,4-dichloro-1-methyl-5-pentafluoroethylpyrrol-3-yl)-4-fluorophenoxy]acetate, 3-[4-chloro-2-fluoro-5-(3-butyn-2-yloxy)phenyl]-2,4-dichloro-1-methyl-5-trifluoromethylpyrrole, 3-[4-chloro-2-fluoro-5-(2-propynyloxy)phenyl]-2,4-dichloro-1-methyl-5-pentafluoroethylpyrrole, 3-[4-chloro-2-fluoro-5-(2-propynyloxy)phenyl]-2,4-dichloro-1-ethyl-5-trifluoromethylpyrrole, and ethyl [2-chloro-5-(-2,4-dichloro-1-ethyl-5–5-trifluoromethylpyrrol-3-yl)-4-fluorophenoxy]acetate.

9. The method according to claim 7, wherein said herbicidal compositions further comprise solid carriers, liquid diluents or surface-active agents.

10. the method according to claim 7, wherein the one or more pyrrolic compound is distributed on the ground at a dose ranging from 1 to 1000 g per hectare.

11. A herbicidal composition comprising solid carriers, liquid diluents or surface-active agents and at least one of the compounds according to claim 6.

12. The method according to claim 8, wherein said herbicidal compositions further comprise solid carriers, liquid diluents or surface-active agents.

13. The method according to claim 8, wherein the one or more pyrrolic compound is distributed on the ground at a dose ranging from 1 to 1000 g per hectare.

* * * * *

UNITED STATES PATENT AND TRADEMARK OFFICE
CERTIFICATE OF CORRECTION

PATENT NO.    : 6,391,827 B1
DATED         : May 21, 2002
INVENTOR(S)   : Meazza et al.

It is certified that error appears in the above-identified patent and that said Letters Patent is hereby corrected as shown below:

<u>Title page,</u>
Item [30], the Foreign Application Priority Data should read:

-- [30]         Foreign Application Priority Data
Jun. 17, 1999    (IT) …………………………….. MI99 A 001347 --

Signed and Sealed this

Fifth Day of November, 2002

Attest:

JAMES E. ROGAN
Attesting Officer        Director of the United States Patent and Trademark Office